United States Patent [19]
Jullian et al.

[11] Patent Number: 5,863,315
[45] Date of Patent: Jan. 26, 1999

[54] PROCESS FOR THE SEPARATION OF ISOALKANES/N-ALKANES BY GAS PHASE ADSORPTION USING A PRESSURE SWING AND FOUR ADSORBERS

[75] Inventors: Sophie Jullian, Rueil Malmaison; Jean-Louis Ambrosino, Montesson; Alain Chansolme, Chatou; Valerie Wiss-Henrard, Viroflay, all of France

[73] Assignee: Institut Francais du Petrole, France

[21] Appl. No.: 900,532

[22] Filed: Jul. 25, 1997

[30] Foreign Application Priority Data

Jul. 26, 1996 [FR] France ............................. 96 09551

[51] Int. Cl.⁶ ..................................................... B01D 53/047
[52] U.S. Cl. ................................ 95/98; 95/100; 95/103; 95/105; 95/143; 585/829
[58] Field of Search ..................... 95/96–98, 100–105, 95/143; 585/822, 829

[56] References Cited

U.S. PATENT DOCUMENTS

| | | | |
|---|---|---|---|
| Re. 29,941 | 3/1979 | Bird .......................................... | 95/98 X |
| 2,944,092 | 7/1960 | Feldbauer, Jr. et al. ..................... | 95/97 |
| 2,978,407 | 4/1961 | Tuttle et al. .............................. | 95/97 X |
| 3,226,914 | 1/1966 | Griesmer et al. ........................... | 95/98 |
| 3,409,544 | 11/1968 | Cottle ....................................... | 585/822 |
| 3,430,418 | 3/1969 | Wagner ....................................... | 95/100 |
| 4,077,779 | 3/1978 | Sircar et al. .............................. | 95/101 X |
| 4,176,053 | 11/1979 | Holcombe ............................ | 585/822 X |
| 4,299,596 | 11/1981 | Benkmann ............................. | 95/143 X |
| 4,350,501 | 9/1982 | Bannon .................................. | 95/143 X |
| 4,436,533 | 3/1984 | Bannon ......................................... | 95/98 |
| 4,455,444 | 6/1984 | Kulprathipanja et al. ............ | 95/143 X |
| 4,595,490 | 6/1986 | Gray, Jr. et al. ..................... | 585/822 X |
| 4,608,061 | 8/1986 | Volles et al. ............................... | 95/100 |
| 4,732,578 | 3/1988 | Benkmann ............................... | 95/98 X |
| 5,656,068 | 8/1997 | Smokarek et al. ..................... | 95/102 X |
| 5,733,359 | 3/1998 | Doong et al. ............................ | 95/98 X |

FOREIGN PATENT DOCUMENTS

| | | |
|---|---|---|
| 0 006 665 | 1/1980 | European Pat. Off. . |
| 0 103 070 | 3/1984 | European Pat. Off. . |
| 2 325 624 | 4/1977 | France . |

*Primary Examiner*—Robert Spitzer
*Attorney, Agent, or Firm*—Millen, White, Zelano, & Branigan, P.C.

[57] ABSTRACT

Four adsorbers 1 to 4, each operating in a cycle comprising (described for adsorber 2): an adsorption step 1 wherein a feed from adsorber 2 is circulated to adsorber 2; an adsorption step 2 wherein feed is injected to the bottom of adsorber 2 and a product rich in isoparaffins is recovered from the head of adsorber 2; an adsorption step 3 wherein a portion of the fluid leaving adsorber 2 is sent to adsorber 3; an adsorption step 4 wherein the head of adsorber 2 receiving the feed is connected to the bottom of adsorber 3; a first depressurisation step 5 wherein adsorber 2 at high pressure is connected to adsorber 4 at a lower pressure; a second depressurisation step 6 wherein the head of adsorber 2 is closed; a stripping step 7 wherein the bottom of adsorber 2, which receives desorbent overhead, is connected to the top of adsorber 2; two principal stripping steps 8 and 9 wherein adsorber 2 alone is supplied with desorbent; a stripping finishing step 10 wherein adsorber 2 is continued to be supplied with desorbent and the outlet from the adsorber 2 is connected to adsorber 3; a first pressurisation step 11 to an intermediate pressure wherein the bottoms of adsorbers 2 and 4 are connected together; and a second pressurisation step 12 wherein a stream providing a portion of the effluent from adsorber 1 is introduced into the bottom of adsorber 2.

11 Claims, 3 Drawing Sheets

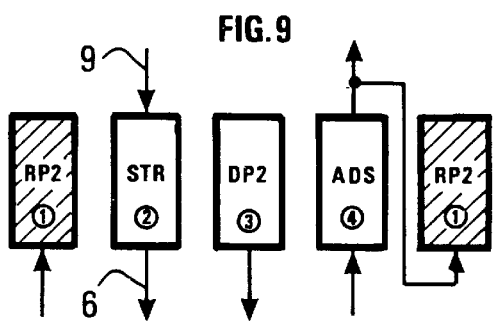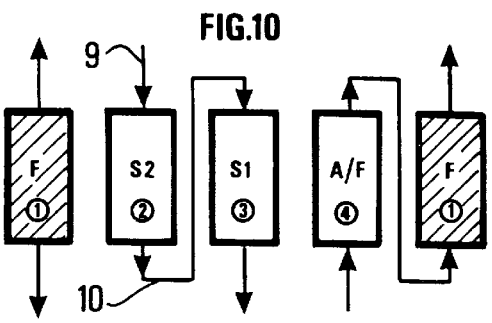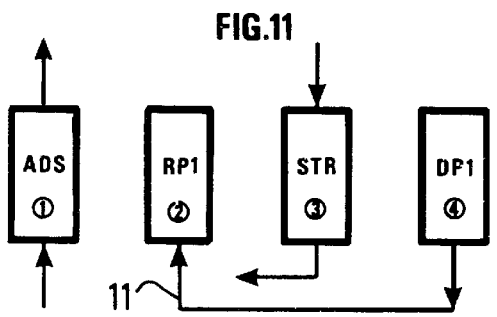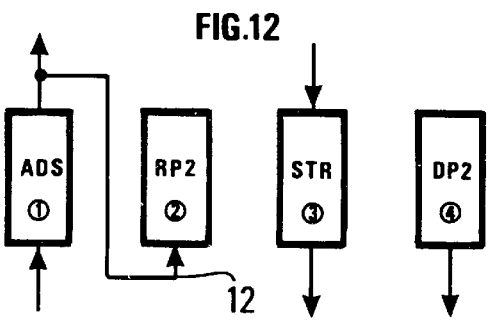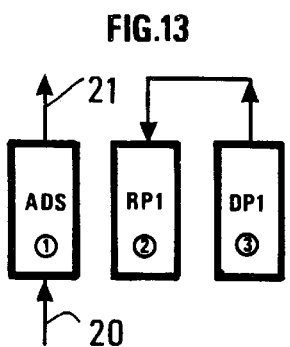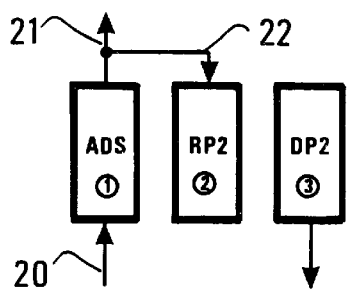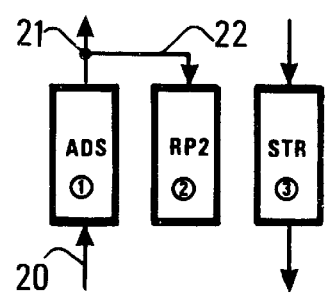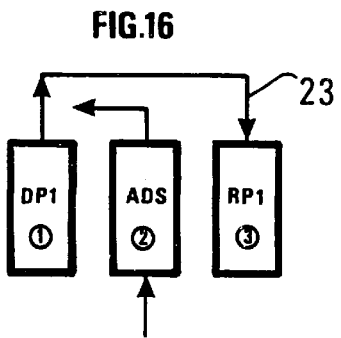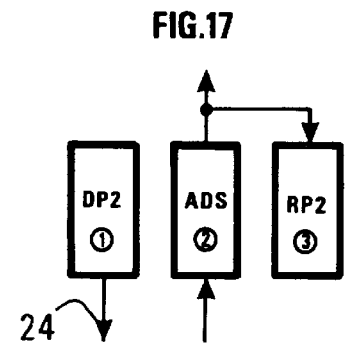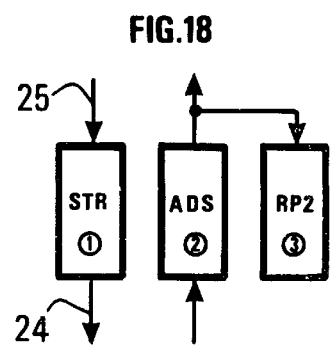

PROCESS FOR THE SEPARATION OF ISOALKANES/N-ALKANES BY GAS PHASE ADSORPTION USING A PRESSURE SWING AND FOUR ADSORBERS

The present invention concerns an adsorption process, more particularly a vapour phase adsorption process using separation mechanisms based on the phenomena of exclusion or adsorption difference.

More particularly, it concerns a separation process which judiciously uses trains of sequences in a PSA to reduce problems due to the matter transfer zone.

The present invention is suitable for separation by adsorption on a zeolitic sieve of a mixture of linear paraffins and a mixture of non linear paraffins, more particularly the separation of isoparaffins and normal paraffins from a hydrocarbon feed containing them. Still more particularly, the hydrocarbon feed to be treated originates from isomerisation of a C5/C6 hydrocarbon cut.

PSA (Pressure Swing Adsorption) is an adsorption process in which a gaseous mixture is brought into contact with a fixed bed of adsorbent at high pressure to eliminate certain "adsorbable" constituents from the mixture. Even if desorption can be effected by different means, the common characteristic of PSA is to regenerate the bed by depressurisation and, in some cases, by low pressure stripping.

Such PSA processes have enjoyed considerable success in the natural gas industry, in separating the components of air, in the production of solvents and in different sectors of refining. A review of the important steps in the development of PSA was carried out in 1984 in an article in the AIChE Symposium Series entitled "Twenty Five Years' Progress in Adiabatic Adsorption Processes" by R. T. Cassidy and E. S. Holmes.

PSA separation processes constitute an economic and efficient means of separating the constituents of a gas containing at least two components having different adsorption characteristics. The adsorbable constituent may be an impurity to be eliminated from the less adsorbable constituent, the latter then being recovered as the product. Alternatively, the more adsorbable product is that which is desired and must be separated from the less adsorbable constituent. As an example, carbon monoxide and light compounds may be required to be eliminated from a hydrogen-rich stream to produce hydrogen with a purity of more than 99% for use in hydrocracking or any other catalytic process in which the catalyst is sensitive to impurities. On the other hand, the more adsorbable product may be that which is to be recovered, such as ethylene from a feed to obtain an ethylene-rich product.

In the most conventional PSA cases, a gaseous multi-component feed is introduced into at least one of the adsorbent beds at a high effective pressure to adsorb at least one of the constituents (the adsorbed fraction), while the other constituents (the non adsorbed fraction) pass through the bed without being retained. At a predetermined time, the stream of feed to the adsorber is interrupted and the bed is depressurised by carrying out one or more co-current depressurisation steps (in this description, the flow direction is always that of adsorption), until a predefined pressure is reached. This allows the less adsorbable compounds or those remaining in the adsorption zone (interstitial volumes) to be evacuated without being mixed with the most adsorbable constituent. The gas recovered during these depressurisation steps is generally used to carry out the steps of pressure equalisation or subsequent stripping. In the prior art and in the present description, the term "pressure equalisation" is used to describe the connection of a high pressure adsorber to a low pressure adsorber, made until the same pressure is obtained in the two adsorbers. The bed is then depressurised in counter-current mode and often stripped to desorb the most strongly adsorbed compound of the feed and to evacuate that gas from the bed before the steps of pressurisation then adsorption. Such processes are described, for example, in United States U.S. Pat. No. 3,430,418 or in the more general work by R. T. Yang: "Gas Separation by Adsorption Processes", Boston, Butterworth (1987), in which cycles based on the use of several beds are described in detail. In general, and as described in the publications mentioned above, PSA type processes are carried out sequentially by alternate use of all of the adsorption beds.

The selectivities used in PSA processes depend on three basic mechanisms: diffusional selectivity, form (or exclusion) selectivity and energetic selectivity.

In the case of diffusional selectivity, the driving force for separation is the difference in adsorption rate, desorption rate and diffusion rate of the different compounds in the mixture of gases to be separated.

In the case of form (or geometric) selectivity, separation is effected on the basis of the size of the different molecules to be separated with respect to that of the micro-pores of the adsorbent. The largest molecules do not penetrate into the porosity of the adsorbent, while the smallest are adsorbed: this is the sieving effect and the dimension of the pores in the adsorbent determine which compounds will adsorb and which will not adsorb.

As regards energetic selectivity, the affinity of the adsorbent or the forces relative to adsorption for one or other of the compounds controls separation. The least strongly adsorbed compound becomes the non adsorbable fraction and the most strongly adsorbed compound becomes the adsorbable fraction.

In the case of processes based on diffusional or geometric selectivities, the matter transfer rate is of importance as regards the efficacity and the size of the beds. Because of this phenomenon, a concentration profile for the adsorbate exists in the bed as the adsorption front progresses through it. The term "matter transfer zone" (MTZ) is known to the skilled person and refers to the region containing this profile. In this region, the concentration of adsorbate is zero at one extremity (towards the bed outlet) and equal to that in the feed at the other (towards the feed inlet). With the aim of producing a high pressure, high purity stream, the PSA adsorption cycle is determined such that this matter transfer zone does not leave the bed. This means that the adsorbent in the MTZ is not saturated to its equilibrium capacity and there is thus a loss of efficiency in the system. Many studies have been made concerning reducing the matter transfer zone by acting on the hydrodynamic parameters of the system. Reduction of this matter transfer zone and thus of the unused portion of the bed results in a reduction in the quantity of adsorbent and thus in the size of the beds.

SUMMARY OF THE INVENTION

One aim of the invention is to provide a means of reducing the size of the bed, or conversely to increase the dynamic capacity of the adsorbent, in the case of conventional PSA processes using geometric type selectivity. This increase in capacity is effected with no (or with a minor) increase in investment or in operating costs.

It has been discovered that for a given separation, the quantity of sieve to be used can be reduced by judicious arrangement of the sequences. This increase in performance can be analysed in different ways: either in terms of an increase in dynamic capacity, or in terms of an increase in HSV (hourly space volume) for a given performance. This is due to the fact that, because of the arrangement of sequences undergone by the different adsorbers, which sequences will be described below, at the end of the adsorption step the bed is completely saturated by the adsorbable compound(s), i.e., the matter transfer zone has left the adsorber before the latter is regenerated.

The process of the present invention can be applied to the production of a mixture which is rich in isoparaffins to produce a high octane number product from a mixture which also contains normal paraffins.

BRIEF DESCRIPTION OF THE DRAWINGS

The process of the invention will be described below with reference to Table 1 below and to the accompanying FIGS. 1 to 12 which illustrate sequences 1 to 12 respectively. Conversely, FIGS. 13–21, for purposes of comparison, relate to three adsorbers instead of four, illustrating sequences 1 to 9.

The invention thus provides a process for the separation of n-paraffins and isoparaffins from a mixture containing these compounds, by gas phase adsorption of the n-paraffins, the process using four adsorbers which are numbered 1 to 4 below, of substantially the same size and operating in at least one cycle of steps which will be described below with reference to adsorber 2 of FIGS. 1 to 12. More particularly, the treated mixture originates from the isomerisation of C5/C6 hydrocarbons.

Figure 1:
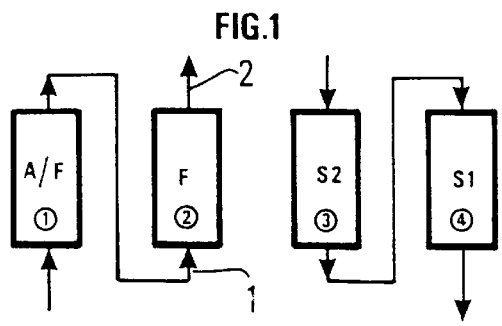
Figure 2:
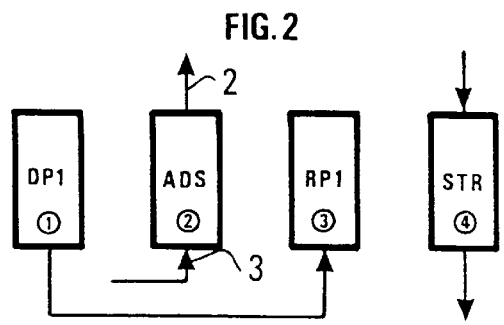
Figure 3:
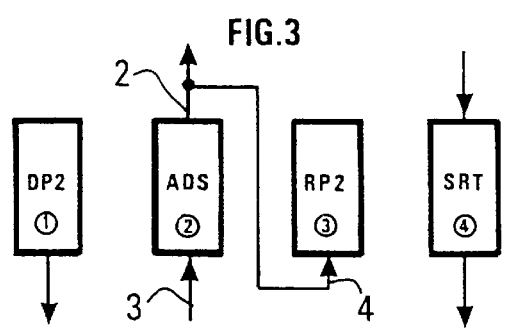
Figure 4:
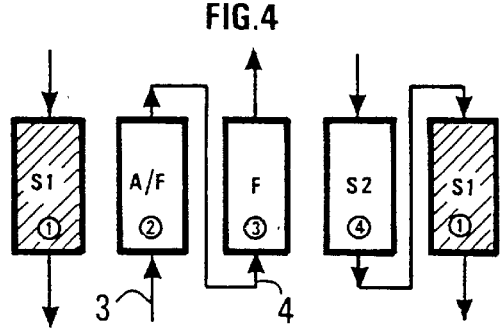
Figure 5:
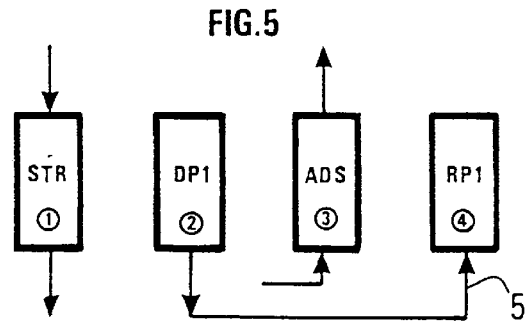
Figure 6:
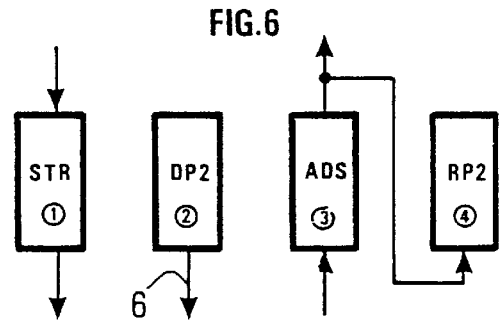
Figure 7:
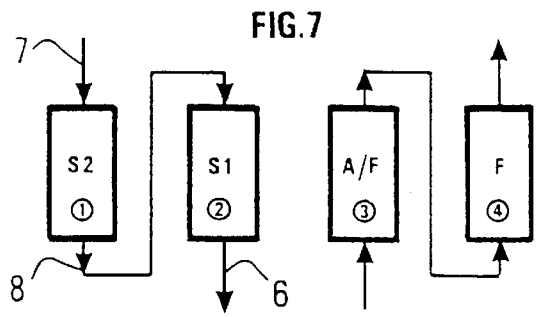
Figure 8:
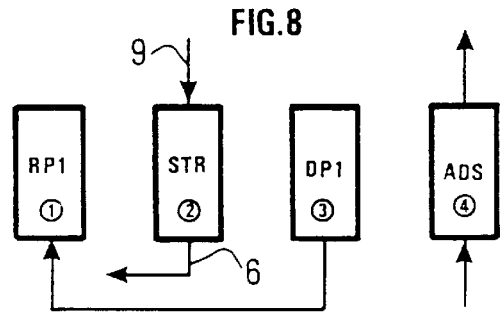

ously in the second pressurisation phase. During this step, adsorber 2 receiving feed via line 3 is saturated with n-paraffins and the matter transfer zone is displaced towards the following adsorber 3, connected in series.

e) Sequence 5: A first depressurisation (DP1) step is carried out by connecting via line 5 the bottom of adsorber 2, functioning at high pressure, with the bottom of adsorber 4 which, having finished its stripping step, is at a lower pressure. This equilibrates the pressure in adsorbers 2 and 4. The adsorbent in adsorber 2 is thus completely saturated with feed at equilibrium.

f) Sequence 6: A second depressurisation step (DP2) is carried out, the upper extremity of adsorber 2 being closed; if the feed which is treated by the process originates from an isomerisation unit, for C5/C6 hydrocarbons for example, the bottom of adsorber 2 can be connected via line 6 with the circuit which recycles to the isomerisation step, which is at low pressure.

g) Sequence 7: In a first stripping step (S1), the bottom of the preceding adsorber 1 is connected to the top of adsorber 2 via line 8, desorbent is injected via line 7 to the head of adsorber 1 which is finishing stripping (S2); the effluent which leaves is then relatively depleted in adsorbable fraction. The stripping phase (S1) generally takes place at a pressure of less than 5 bars, preferably less than 3 bars absolute and is carried out counter-current to the adsorption step. The product leaving via line 6 of adsorber 2 essentially consists of a fraction which is rich in n-paraffins. If the feed which is treated by the process originates from an isomerisation unit, for C5/C6 hydrocarbons for example, the effluent can be recycled to the isomerisation unit.

TABLE 1

| SEQUENCE | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| BED 1 | A/F | DP1 | DP2 | S1 | STRIPPING | | S2 | RP1 | RP2 | F | ADSORPTION | |
| BED 2 | F | ADSORPTION | | A/F | DP1 | DP2 | S1 | STRIPPING | | S2 | RP1 | RP2 |
| BED 3 | S2 | RP1 | RP2 | F | ADSORPTION | | A/F | DP1 | DP2 | S1 | STRIPPING | |
| BED 4 | S1 | STRIPPING | | S2 | RP1 | RP2 | F | ADSORPTION | | A/F | DP1 | DP2 |

In the following description, the terms "bed" and "adsorber" will be used without discrimination to designate the adsorption beds, even when the bed under consideration is not in its adsorption phase.

The characteristic cycle of the process of the invention can be defined as follows.

a) Sequence 1: In an adsorption step (F), a feed constituted by effluent from the preceding adsorber (adsorber 1) is circulated in upflow mode in adsorber 2. The outlet from adsorber 1, in the adsorption phase, is connected in series with the bottom of adsorber 2 via line 1. The fluid is in upflow mode in the two adsorbers. The isoparaffin-rich product is recovered from the upper portion of adsorber 2 via line 2.

b) Sequence 2: In an adsorption step (ADS), the feed is directly injected via line 3 as an upflow into the bottom of adsorber 2. The isoparaffin-rich product is recovered from the upper portion of adsorber 2 via line 2.

c) Sequence 3: The adsorption operation (ADS) is continued and a portion of the isoparaffin-rich outlet fluid is extracted from line 2 via line 4 to carry out the second pressurisation step RP2 of the following adsorber 3, in upflow mode.

d) Sequence 4: The adsorption step (A/F) is continued and the upper extremity of adsorber 2 is connected via line 4 to the bottom of the following adsorber (adsorber 3), previh) Sequences 8 and 9: In the principal stripping step (STR), adsorber 2 alone is supplied with a downflow of desorbent via line 9. In this case again, the effluent leaving via line 6 can be recycled to the isomerisation unit.

i) Sequence 10: In the stripping finishing step (S2), adsorber 2 continues to be supplied with desorbent via line 9, but the outlet from adsorber 2 is connected via line 10 to the following adsorber 3 which is starting the desorption phase (S1).

j) Sequence 11: Pressurisation (RP1) from the low pressure to an intermediate pressure by connecting the bottoms of adsorbers 2 and 4 via line 11.

k) Sequence 12: Finally, a second pressurisation step (RP2) is carried out to the adsorption pressure by means of a stream formed by part of the effluent from the preceding adsorber 1 via line 12, which is operating in an adsorption step (ADS). Fluid is introduced into the lower portion of adsorber 2 to avoid polluting the bed if this fluid is not completely free of adsorbable products.

In summary, n-paraffins are adsorbed at high pressure (steps F and ADS) and desorbed at a lower pressure by means of pressure reduction combined with elimination by "stripping" using a gas stream which is rich in isoparaffins. The desorbent can contain an n-paraffin concentration which is in the range 0 to 20%.

The adsorbent bed is generally constituted by a molecular sieve based on zeolite which can selectively adsorb n-paraffins and which has an apparent pore diameter of approximately 5 Angstroms. 5A zeolite is suitable: it has a pore diameter which is close to 5 Å and it has a large n-paraffin adsorption capacity. However, other adsorbents such as chabazite or erionite can be used.

The preferred operating conditions are temperatures of 100° C. to 400° C. or more, preferably 200° C. to 300° C., with an adsorption pressure of 5 to 40 bars or more, preferably 15 to 25 bars. The adsorption cycle generally has a duration of 2 to 5 minutes, preferably 4 to 6 minutes.

Non limiting Example 1 below illustrates the invention. Example 2 is given by way of comparison.

EXAMPLE 1

The process of the invention was carried out in a unit comprising four identical adsorbers operating in the cycle described above.

The adsorbers were cylinders which had a 0.053 m internal diameter and which were 4.77 m high, each containing 8.05 kg of 5A sieve. The feed and desorbent were introduced at a temperature which was kept at 215° C.

The feed was constituted by a light naphtha and originated from isomerisation of a C5/C6 petroleum cut with the following composition by weight:

| Constituent | % by weight |
| --- | --- |
| Isobutane (iC4) | 1.39 |
| Normal butane (nC4) | 1.02 |
| Isopentane (iC5) | 27.99 |
| Normal pentane (nC5) | 11.2 |
| 2,2-dimethylbutane (22DMB) | 11.3 |
| 2,3-dimethylbutane (23DMB) | 4.8 |
| 2-methylpentane (2MC5) | 14.6 |
| 3-methylpentane (3MC5) | 8.7 |
| Normal hexane (nC6) | 6.1 |
| Cyclopentane (CC5) | 2.0 |
| Methylcyclopentane (MC5) | 5.7 |
| Cyclohexane (CC6) | 5.2 |
| TOTAL | 100.00 |

The feed and desorbent were supplied to the separation unit at a controlled flow rate and the effluents were recovered at a controlled pressure.

The feed flow rate was 19.65 kg/h; its octane number (RON) was 81.6.

The desorbent flow rate was 6.74 kg/h; it had the following composition by weight:

| Constituent | % by weight |
| --- | --- |
| Isobutane (iC4) | 4.25 |
| Normal butane (nC4) | 3.39 |
| Isopentane (iC5) | 92.26 |
| Normal pentane (nC5) | 0.1 |
| TOTAL | 100.00 |

The adsorption pressure was in the range 17.7 to 17.1 bars absolute, while the desorption pressure was 2.6 bars absolute.

The duration, in seconds, of the different sequences of the cycle is shown in the table below for a quarter of the cycle:

| | Sequence | | |
| --- | --- | --- | --- |
| | 1 | 2 | 3 |
| bed1 | A/F | DP1 | DP2 |
| bed2 | F | ADS | ADS |
| bed3 | S2 | RP1 | RP2 |
| bed4 | S1 | STR | STR |
| Duration (sec) | 60 | 40 | 100 |

The overall duration of the adsorption phase for one bed was equal to the sum of sequences F and ADS, in this case 200 seconds. This sum also corresponded to the total duration of desorption for a given adsorber, the sum of sequences STR and S1.

It should be noted that, because the desorbent always fed an adsorber, it was not necessary to provide the unit with a by-pass valve (as was the case for comparative Example 2 below).

The balances for the unit were produced in the converging cyclic state, i.e., such that two successive balances led to the same result.

The isoparaffin-rich effluent was given the designation "IPSORBAT". It had the average composition by weight cumulated over one hour of operation given below:

| Constituent | % by weight |
| --- | --- |
| Isobutane (iC4) | 1.32 |
| Normal butane (nC4) | 1.81 |
| Isopentane (iC5) | 36.49 |
| Normal pentane (nC5) | 1.13 |
| 2,2-dimethylbutane (22DMB) | 12.67 |
| 2,3-dimethylbutane (23DMB) | 5.38 |
| 2-methylpentane (2MC5) | 16.38 |
| 3-methylpentane (3MC5) | 9.77 |
| Normal hexane (nC6) | 0.59 |
| Cyclopentane (CC5) | 2.24 |
| Methylcyclopentane (MC5) | 6.39 |
| Cyclohexane (CC6) | 5.83 |
| TOTAL | 100.00 |

The "IPSORBAT" flow rate was 14.17 kg/h; this product had an octane number (RON) of 88.0.

EXAMPLE 2 (comparative)

Figure 19:
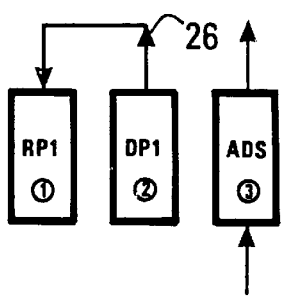
Figure 20:
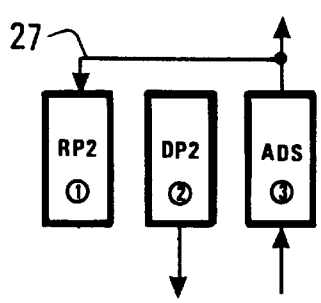
Figure 21:
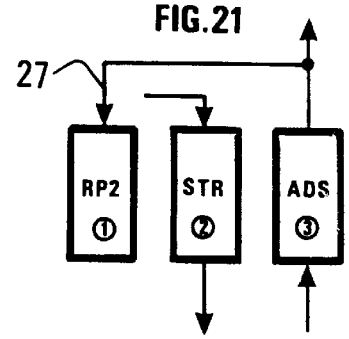

This differed from the preceding example in that it used three adsorbers instead of four and the unit operated using a known cycle, described below in conjunction with Table 2 and FIGS. 13 to 21, which illustrate sequences 1 to 9 respectively.

TABLE 2

| SEQUENCE | 1 | 2 | 3 | 4 | 5 | 6 | 7 | 8 | 9 |
| --- | --- | --- | --- | --- | --- | --- | --- | --- | --- |
| BED 1 | ADS | ADS | ADS | DP1 | DP2 | STR | RP1 | RP2 | RP2 |
| BED 2 | RP1 | RP2 | RP2 | ADS | ADS | ADS | DP1 | DP2 | STR |

TABLE 2-continued

| SEQUENCE | 1 | 2 | 3 | 4 | 5 | 6 | 7 | 8 | 9 |
|---|---|---|---|---|---|---|---|---|---|
| BED 3 | DP1 | DP2 | STR | RP1 | RP2 | RP2 | ADS | ADS | ADS |
| Duration (sec) | 40 | 50 | 110 | 40 | 50 | 110 | 40 | 50 | 110 |

The cycle followed by each adsorber took place in nine sequences. These sequences were identical for the three adsorbers, but displaced in time by a duration equal to a third of the overall duration of the cycle. Bed 1, for example, underwent the following sequences:

a sequence 1 in which a high pressure adsorption step (ADS) was carried out by introducing feed to the bottom of bed 1 via line 20 and passing it as an upflow through said bed, the product leaving overhead via line 21;

two sequences 2 and 3 in which the adsorption step (ADS) was continued as an upflow and a portion of the effluent leaving adsorber 1 via line 21 was recovered and sent via line 22 to the following adsorber 2 to carry out the second pressurisation (RP2) therein;

a sequence 4 in which pressure equilibration (DP1) took place by connecting the upper extremities of adsorber 1 and adsorber 3 via line 23, adsorber 3 being at the end of its stripping step (STR) to start repressurisation therein;

a sequence 5 in which a second depressurisation step (DP2) took place by connecting the bottom portion of adsorber 1 with a circuit which recycled to the isomerisation unit via line 24;

a sequence 6 in which a stripping step (STR) was carried out by introducing desorbent into bed 1 as a downflow via line 25, the effluent which left, containing adsorbed n-paraffins, being recycled via line 24 to the isomerisation unit;

a sequence 7 in which a pressurisation step (RP1) was carried out by connecting bed 1 with bed 2 via line 26; and two sequences 8 and 9 in which a second pressurisation step (RP2) was carried out by connecting bed 1 with bed 3 via line 27, the latter bed carrying out an adsorption step (ADS).

Each adsorber had an internal diameter of 0.053 m and a height of 6.36 m and contained 10.7 kg of 5A sieve. Thus the same total weight of sieve was used. The compositions and feed and desorbent flow rates were the same as for Example 1, in accordance with the invention. The same was true for the inlet temperatures.

The adsorption pressures were in the range 17.7 to 17.4 bars absolute and the desorption pressure was 2.6 bars absolute.

The duration of the different cycles is shown in table 2, one cycle being carried out in 600 seconds. It should be noted that the durations of the adsorption and pressure equilibration sequences (DP1/RP1) were the same as those in Example 1, in accordance with the invention. However, a by-pass had to be provided for the unit during the sequences when desorbent was not used (DP1/DP2).

The effluent recovered from the process, which was rich in isoparaffins, had the following average composition by weight, cumulated over one hour of operation:

| Constituent | % by weight |
|---|---|
| Isobutane (iC4) | 1.78 |
| Normal butane (nC4) | 1.31 |
| Isopentane (iC5) | 36.08 |
| Normal pentane (nC5) | 2.45 |
| 2,2-dimethylbutane (22DMB) | 12.33 |
| 2,3-dimethylbutane (23DMB) | 5.24 |
| 2-methylpentane (2MC5) | 15.93 |
| 3-methylpentane (3MC5) | 9.50 |
| Normal hexane (nC6) | 1.31 |
| Cyclopentane (CC5) | 2.18 |
| Methylcyclopentane (MC5) | 6.22 |
| Cyclohexane (CC6) | 5.67 |
| TOTAL | 100.00 |

The IPSORBAT flow rate was 13.77 kg/h and had an octane number (RON) of 87.3.

Comparison of the results of Example 1 in accordance with the invention and comparative Example 2 show that the gain in octane number is larger using the process of the invention since in this latter case, an octane number of 88.0 was obtained.

We claim:

1. A process for separating n-paraffins and isoparafins by gas phase adsorption of a hydrocarbon feed originating from an isomerisation step, said process being characterized in that it uses four adsorbers, numbered 1 to 4, with substantially the same size and each operating in at least one cycle of steps which, described with reference to adsorber 2, comprise:

a) a sequence 1 in which an adsorption step (F) is carried out, by circulating a feed constituted by the effluent from preceding adsorber 1 through adsorber 2 as an upflow, by connecting the outlet from adsorber 1, in its adsorption phase, in series with the bottom of adsorber 2;

b) a sequence 2, in which an adsorption step (ADS) is carried out, by directly injecting the feed as an upflow into the bottom of adsorber 2 and recovering a product which is rich in isoparaffins from the upper portion of adsorber 2;

c) a sequence 3 in which the adsorption operation (ADS) is continued and a portion of an isoparaffin-rich outlet fluid is extracted to carry out a second pressurisation step RP2 of the following adsorber 3, in upflow mode;

d) a sequence 4 in which the adsorption step (A/F) is continued by connecting the upper extremity of adsorber 2 to the bottom of the following adsorber 3, previously in the second pressurisation phase, adsorber 2 receiving the feed thus being saturated with n-paraffins and the matter transfer zone being displaced towards the following adsorber 3, connected in series;

e) a sequence 5 in which a first depressurisation step (DP1) is carried out by connecting the bottom of adsorber 2 operating at high pressure with the bottom of adsorber 4, which has finished its stripping step and is at a lower pressure, thus equilibrating the pressure in adsorbers 2 and 4;

f) a sequence 6 in which a second depressurisation step (DP2) is carried out, the upper extremity of adsorber 2 being closed;

g) a sequence 7 in which a first stripping phase (S1) is carried out by connecting the bottom of the preceding adsorber 1 in series with the top of adsorber 2, by injecting desorbent into the head of adsorber 1 which is at the end of the stripping step (S2), the effluent which leaves therefrom then being relatively depleted in the adsorbable fraction, the product leaving adsorber 2 essentially consisting of a fraction which is rich in n-paraffins;

h) two sequences 8 and 9 in which the principal stripping step (STR) is carried out by supplying adsorber 2 alone with a downflow of desorbent;

i) a sequence 10 in which a stripping finishing step (S2) is carried out by continuing to supply adsorber 2 with desorbent and by connecting the outlet from said adsorber 2 to the following adsorber 3, which is beginning its desorption phase (S1);

j) a sequence 11 in which pressurisation (RP1) is carried out from the low pressure to an intermediate pressure by connecting adsorbers 2 and 4 at the bottom; and k) a sequence 12 in which a second pressurisation (RP2) is carried out to the adsorption pressure by means of a stream which originates from part of the effluent from the preceding adsorber 1, which operates in an adsorption step (ADS), the fluid being introduced to the lower portion of adsorber 2.

2. A process according to claim 1, wherein in that in sequences 7 to 10, stripping is carried out using a stream of isoparaffin-rich gas.

3. A process according to claim 2, wherein the proportion of n-paraffins contained in the desorbent is in the range 0 to 20%.

4. A process according to any one of claim 1, characterized in that the adsorbent bed is constituted by a molecular sieve based on zeolite which is capable of selectively adsorbing n-paraffins and with an apparent pore diameter which is approximately 5 Angstroms.

5. A process according to claim 4, wherein the adsorbent bed is constituted by 5A zeolite, chabazite or erionite.

6. A process according to any one of claim 1, carried out at temperatures of 100° C. to 400° C. and at an adsorption pressure of 5 to 40 bars, the adsorption cycle having a duration of 2 to 15 minutes.

7. A process according to claim 6, carried out at temperatures of 200° C. to 300° C. and at an adsorption pressure of 15 to 25 bars, the adsorption cycle having a duration of 4 to 6 minutes.

8. A process according to claim 1, characterized in that in step (g), the stripping phase is carried out at a pressure of less than 5 bars absolute.

9. A process according to claim 1, characterized in that, in step (g), the stripping phase is carried out at a pressure of less than 3 bars absolute.

10. A process according to claim 1, characterized in that the feed which is treated originates from a C5/C6 isomerisation unit.

11. A process according to claim 10, characterized in that in sequences 6, 7, 8 and 9, the desorption effluent from adsorber 12 is recycled to the C5/C6 isomerisation unit by connecting the bottom of adsorber 2 with the circuit which recycles to the isomerisation unit, kept at low pressure.

* * * * *